(12) United States Patent
Roizen et al.

(10) Patent No.: US 8,005,270 B2
(45) Date of Patent: Aug. 23, 2011

(54) SYSTEM AND METHOD FOR DETERMINING AN OBJECTIVE MEASURE OF HUMAN BEAUTY

(75) Inventors: Michael F. Roizen, Shaker Heights, OH (US); Mehmet C. Oz, Cliffstreet Park, NJ (US); Jennifer L. Roizen, Pasadena, CA (US); Jeffrey D. Roizen, Philadelphia, PA (US)

(73) Assignee: Youdocs LLC, Shaker Heights, OH (US)

( * ) Notice: Subject to any disclaimer, the term of this patent is extended or adjusted under 35 U.S.C. 154(b) by 718 days.

(21) Appl. No.: 12/101,190

(22) Filed: Apr. 11, 2008

(65) Prior Publication Data
US 2009/0257654 A1    Oct. 15, 2009

(51) Int. Cl.
G06K 9/00 (2006.01)
G06K 9/46 (2006.01)

(52) U.S. Cl. .......... 382/118; 382/192; 382/203

(58) Field of Classification Search .......... 382/118, 382/192, 203
See application file for complete search history.

(56) References Cited

U.S. PATENT DOCUMENTS

| | | | | |
|---|---|---|---|---|
| 6,091,836 | A * | 7/2000 | Takano et al. | 382/118 |
| 7,286,692 | B2 * | 10/2007 | Kanarat | 382/118 |
| 2005/0144029 | A1 * | 6/2005 | Rakowski et al. | 705/1 |
| 2008/0270175 | A1 * | 10/2008 | Rodriguez et al. | 705/2 |

OTHER PUBLICATIONS

Eisenthal et al. "Facial Attractiveness: Beauty and the Machine" Neural Computation 18, 2006, pp. 119-142.*
Gunes et al. "Assessing Facial Beauty Through Proportion Analysis by Image Processing and Supervised Learning" International Journal of Human-Computer Studies 64, Sep. 15, 2006, pp. 1184-1199.*

* cited by examiner

*Primary Examiner* — Bhavesh Mehta
*Assistant Examiner* — Utpal Shah
(74) *Attorney, Agent, or Firm* — The Marbury Law Group PLLC

(57) ABSTRACT

An objective measure of human beauty is determined by a beauty quantification system. The beauty quantification system comprises a beauty quantification processor, a beauty measure datastore, a beauty score datastore, a user computing device, and a network. The beauty measure datastore comprises quantifiable measures of beauty of a body region. The beauty quantification processor comprises instructions for receiving user data indicative of physical attributes of a selected body region of the user, obtaining measures of beauty from the beauty measures datastore associated with the selected body region, evaluating the user data against the beauty measures of the selected body region, determining a user score indicative of the beauty of the selected body region of the user, storing the user score in the beauty score datastore, and comparing the user score to a score stored in the beauty score datastore. The beauty quantification processor may also suggest enhancements to one or more body regions to improve the user score. The suggested enhancements may be presented as an ordered listed organized by a relative cost benefit measure.

25 Claims, 16 Drawing Sheets

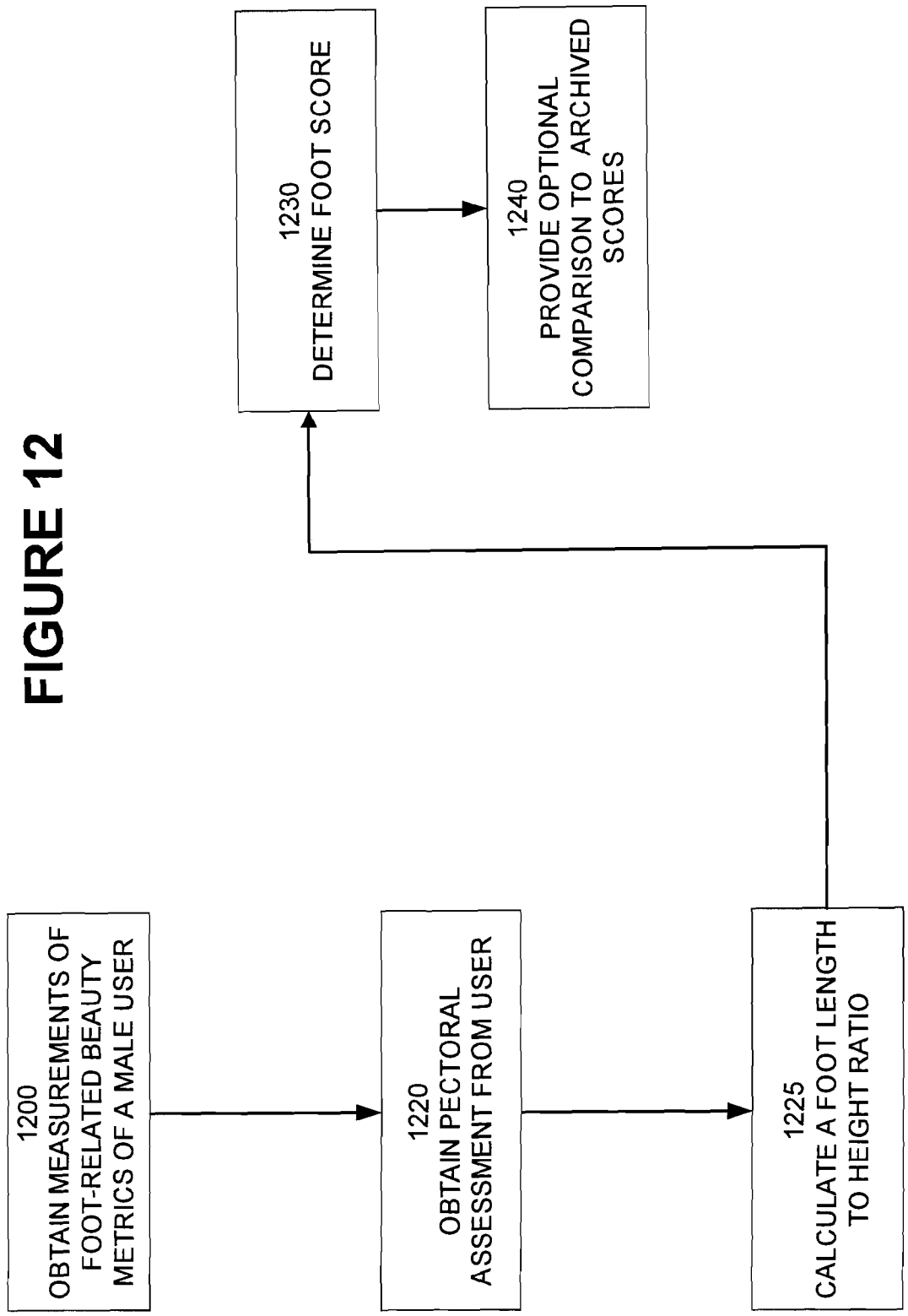

SYSTEM AND METHOD FOR DETERMINING AN OBJECTIVE MEASURE OF HUMAN BEAUTY

BACKGROUND AND SUMMARY

Beauty is commonly defined as a characteristic present in a person, place, object or idea that provides a perceptual experience of pleasure, meaning or satisfaction to the mind or to the eyes, arising from sensory manifestations such as a shape, color, personality, sound, design or rhythm. Beauty is studied as part of aesthetics, sociology, social psychology and culture. Beauty, as a cultural creation, is also extremely commercialized.

In a subjective sense, beauty is determined by characteristics that are perceived in such a way as to provide the "viewer" a feeling of attraction or a sense of well-being. A person, scene, or thing may be perceived as beautiful or ugly by different individuals. In the subjective sense, "beauty exists in the eye of the beholder."

Objective beauty is more difficult to define. Advances in mathematics marked attempts to define beauty in theoretical terms. Symmetry in architecture and objects proportioned according to the golden ratio seemed more attractive. Modern research also suggests that people whose facial features are symmetric and proportioned according the golden ratio are more attractive than those whose faces are not. There is evidence that a preference for beautiful faces emerges early in child development, and that the standards of attractiveness are similar across different cultures.

A strong indicator of physical beauty is "averageness." When images of human faces are averaged together to form a composite image, they become progressively closer to the "ideal" image and are perceived as more attractive. This was first noticed in 1883, when Francis Galton, cousin of Charles Darwin, overlaid photographic composite images of the faces of vegetarians and criminals to see if there was a typical facial appearance for each. When doing this, he noticed that the composite images were more attractive compared to any of the individual images. Researchers have replicated the result under more controlled conditions and found that the computer generated, mathematical average of a series of faces is rated more favorably than individual faces.

Against this background, embodiments of the present invention utilize mathematical models of idealized regions of the body to provide an objective measure of beauty of those regions and of the body as a whole and an objective comparison of an individual's beauty measures to known individuals or groups of individuals.

DESCRIPTION OF THE DRAWINGS

FIG. 12 illustrates the logical flow of a foot evaluation routine for user according to an embodiment.

DETAILED DESCRIPTION

In the discussion that follows, reference is made to the "golden proportion" or "golden ratio." The golden ratio is 1.618 and represented by the lower case greek letter phi, $\phi$. The inverse of $\phi$ is 0.618 and is represented by the upper case greek letter Phi, or $\Phi$.

In an embodiment, a beauty quantification system (BQS) receives images of selected regions of the human body in digital form. The BQS comprises a processor that evaluates the digital images and other data against measures of beauty associated with the selected region and provides a beauty score based on the results. By way of illustration and not as a limitation, beauty scores may be obtained for the face, eyes, nose, lips, hands, upper torso, trunk, legs, and feet. A beauty score may be compared against an absolute standard, against models or people considered to have desirable traits, against people considered to have undesirable traits, or compared to one or more friends or acquaintances.

By way of illustration, in an embodiment, the selected body region is the human face and the BQS receives side and frontal images of a human face in digital form. The BQS evaluates the digital profile images against measures of facial beauty and provides a beauty score based on the results. In an embodiment, the measures of facial beauty comprise a symmetry measure, based on the size and proportions of the facial components (eyes, eyelids, nose, mouth, ears, wrinkles, etc.), the location of the eyes relative to the top third of the face, the location of the nose relative to the middle third of the face, the size of the nose, the proportion of your ears, mouth, eyes, eye lids, chin, wrinkles, etc.

The digital image of the selected region may be modified or augmented and the modified or augmented image evaluated by the BQS to determine the effect of the changes on the beauty score.

Figure 1:
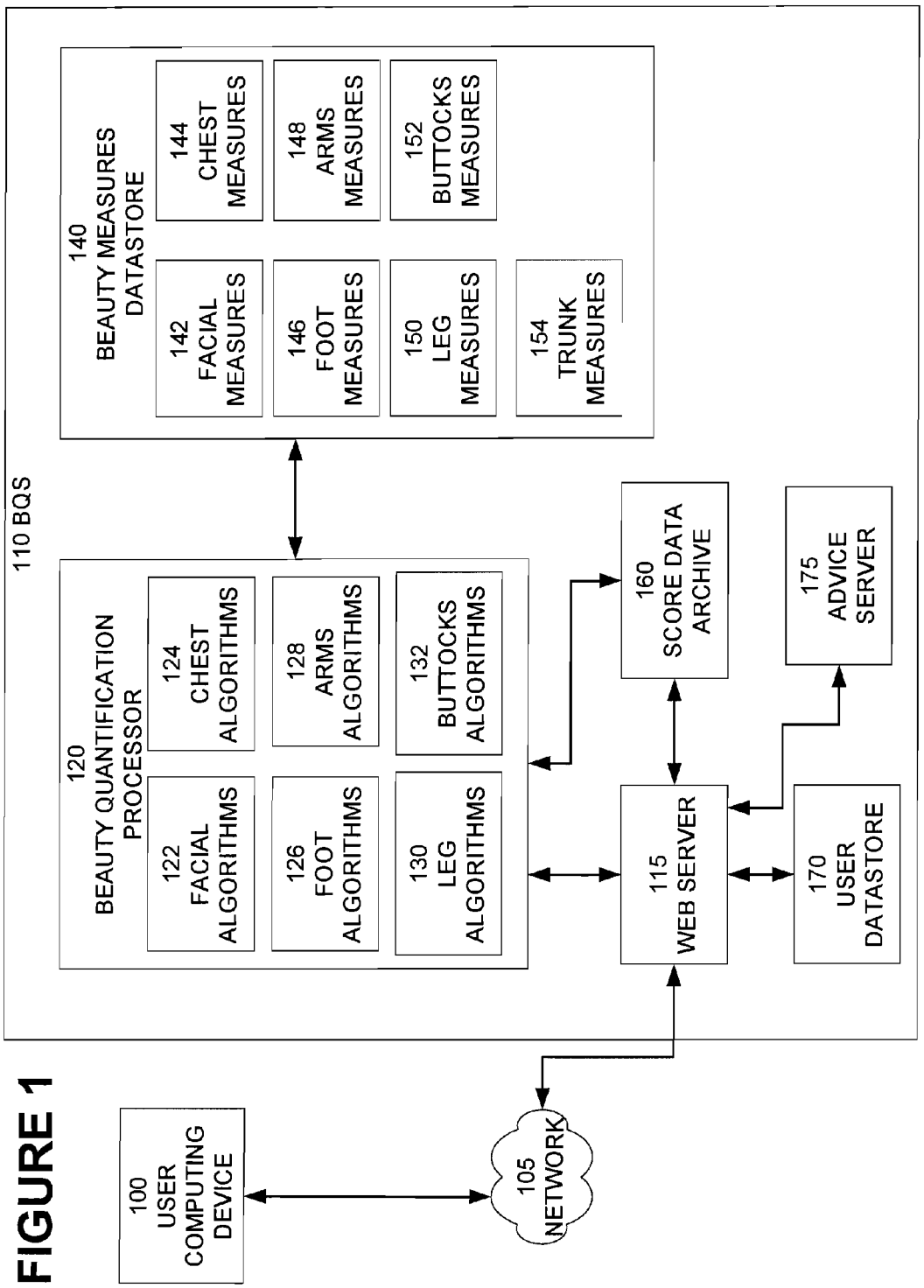
FIG. 1 illustrates the logical elements of a BQS according to an embodiment.

FIG. 1 illustrates the logical elements of a BQS according to an embodiment.

BQS 110 comprises a beauty quantification processor 120 and a beauty measures datastore 140. A user computing device 100 connects to BQS 110 via network 105.

In an embodiment, network 105 is the Internet. However, this is not meant to be a limitation. For example, network 105 may be a local area network such as, for example, a LAN operating at a kiosk in a shopping mall. Alternatively, network 105 may be managed IP network such as, for example, a cable or fiber subscriber access network.

User computing device 100 may be computer, a PDA, a cell phone, or other device capable of sending images over network 105. In an embodiment, user computing device 100 is located at a kiosk in a shopping mall. In yet another embodiment, user computing device 100 is located in a retailer's establishment and enables a customer to access the BQS 110 as a service to assist the customer in selecting clothes, makeup, glasses, tattoos, and other appearance altering items.

Beauty quantification processor 120 receives image data for a selected body region from user computing device 100. The beauty measures for the selected body region are stored in beauty measures datastore 140. The beauty quantification processor 120 retrieves the beauty measures associated with the selected body region from beauty region datastore 140 and applies an algorithm appropriate to the selected body region to the image data and the beauty measures to produce a beauty score.

As illustrated in FIG. 1, beauty measure datastore 140 comprises facial measures 142, chest measures 144, foot measures 146, arms measures 148, leg measures 150, buttocks measures 152 and trunk measures 154. Beauty quantification processor 120 comprises facial algorithms 122, chest algorithms 124, foot algorithms 126, arms algorithms 128, leg algorithms 130, and buttocks algorithms 132. The beauty measures and algorithms illustrated in FIG. 1 are exemplary and not limiting. For example, other measure/algorithm combinations may include skin texture, skin color, finger nails, teeth, lips, hair, hairline, and so on.

Web server 115 provides a web page comprising a graphical user interface (GUI) to user computing device 100. Web server 115 communicates with user datastore 170 to store and retrieve user data, images, results, scores and other related information. In an embodiment, a user is identified by a user identifier. Web server 115 operates with user datastore 170 to permit a user to retrieve previously stored information and to compare the user's scores to the scores of other users identified through the user identifier.

Web server 115 also interacts with beauty quantification processor 120 and with score data archive 160. Score data archive 160 comprises images and scores of celebrities, historical figures, and ideal body components. As described further below, the web server 115 operates with score data archive 160 to permit a user to compare scores of the user with scores of people and models stored in the score data archive 160.

In an embodiment, web server 115 interacts with advice server 175 to provide suggestions for improving scores.

Figure 2:
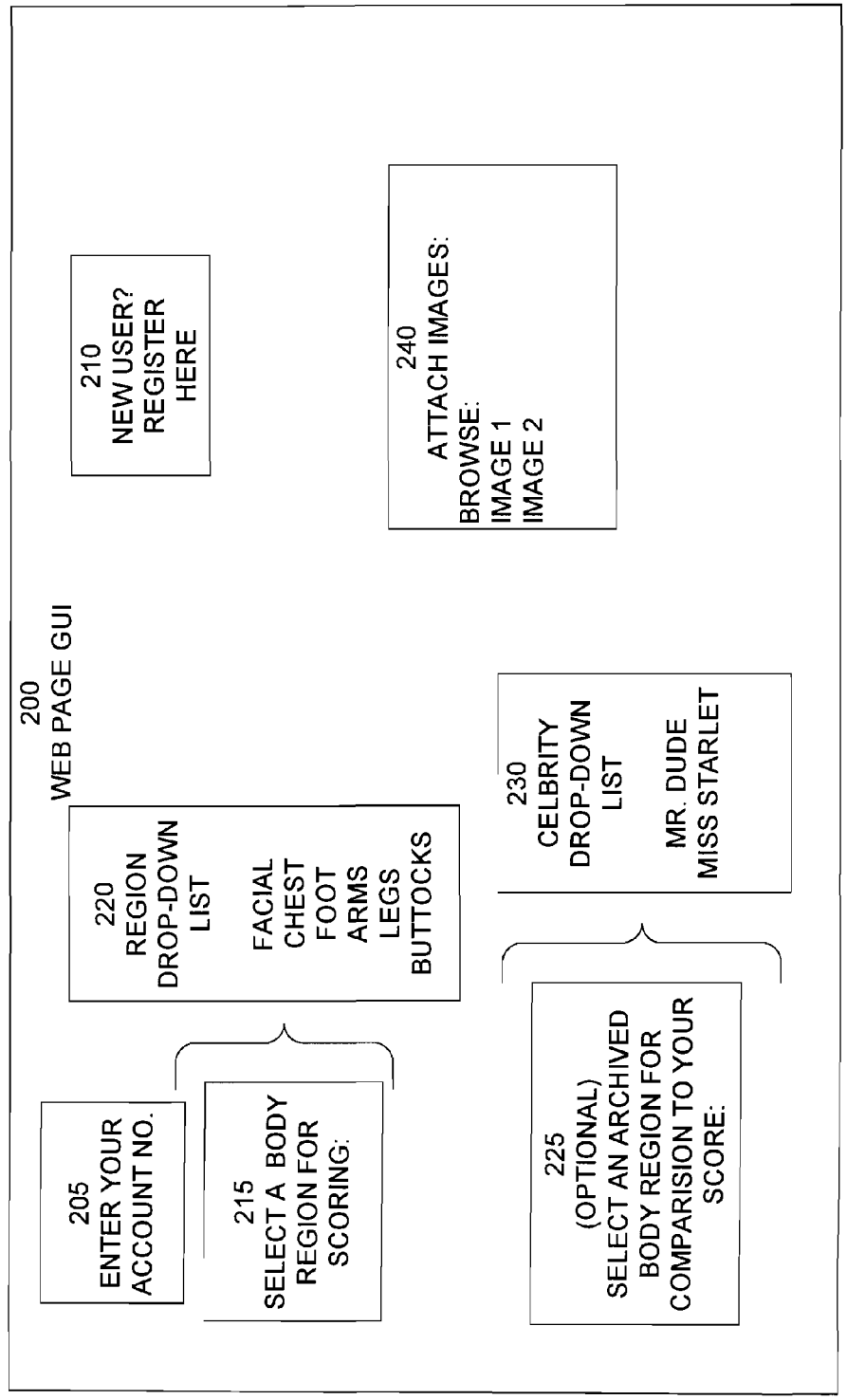
FIG. 2 illustrates a GUI according to an embodiment hereof.

FIG. 2 illustrates a GUI according to an embodiment hereof. Web page GUI 200 provides interactive links for communicating with BQS 110 (FIG. 1). Link 205 permits entry of an account number for a returning user. A new user may register with web server 115 (FIG. 1) using link 210. A user selects a body region for scoring using link 215. Selecting this link causes a region drop-down list 220 to be presented. The user then selects the body region for scoring from the drop-down list. Images relevant to the selected body region are then attached using link 240. Link 240 comprises browse and load functionality to permit a user to find the appropriate images on user input device 100 (FIG. 1) and attach them for sending to web server 115 (FIG. 1).

In an embodiment, a user may optionally use link 225 to select archival data from a drop-down list 230 so that the user's score may be compared with a known data. Archival data may be provided for celebrities, historical figures, or ideal body components.

As described above, a user may change the appearance of a body region and submit digital images of the changed region for quantification by the beauty quantification processor 120. For example, glasses, makeup, and facial contours may be changed to determine what effects the changes may have on the beauty score.

Figure 3:
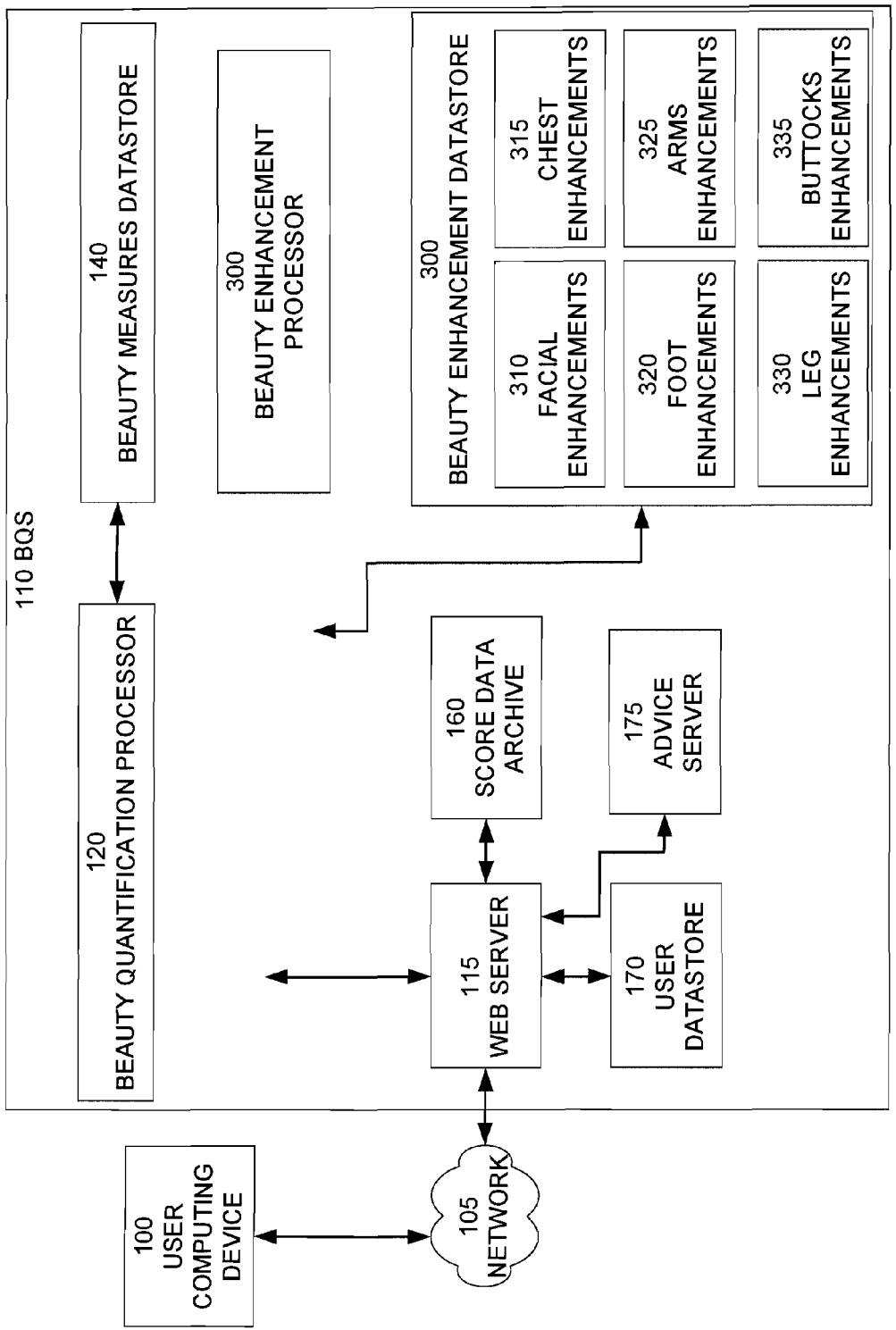
FIG. 3 illustrates the logical elements of a beauty quantification system comprising a beauty enhancement processor according to an embodiment.

FIG. 3 illustrates a beauty quantification system comprising a beauty enhancement processor 300 according to an embodiment that automates and optimizes a beauty score by determining one or more enhancements to a selected body region that are above a specified score value or that improve a score value by a specified amount or percentage. As illustrated, beauty enhancement processor 300 comprises selectable enhancements for the face 310, chest 315, foot 320, arms 325, legs 330 and buttocks 335. However, this is not meant as a limitation. The beauty enhancement processor may provide selectable enhancements for body regions for which beauty scores may be calculated.

By way of illustration, cosmetics can give an illusion of increasing the width of the eye. A canthopexy can increase the apparent width of the eye by elevating and stretching the lateral canthus. Craniofacial surgery can alter the intercanthal distance.

The beauty quantification processor can be configured to provide "before" and "after" scores for selected procedures or make-overs. For example, a user provides facial images for evaluation by the beauty quantification processor 120 and receives a beauty score. The user may select, via a GUI (not illustrated) served by web server 115, enhancements to be added to the provided facial images for evaluation. Thus, the user may select a different shade of lipstick, a different eye treatment, a different pair of glasses, or a cosmetic surgical procedure.

Alternatively, the user may request that beauty enhancement processor 300 select enhancements that affect the beauty score in a certain way. Beauty enhancement processor 300 selects enhancement for the selected body region, in this example, facial enhancements 310, and processes those enhancements through beauty quantification processor 120. The resulting scores and enhancements are provided by web server 115 to user computing device 100.

In an embodiment, the beauty enhancement processor further provides the user an ordered list of the one or more identified enhancements organized by relative improvement in the user score. In still another embodiment, for each of the one or more identified enhancements, the beauty enhancement processor determines a cost benefit measure indicative of a unit of improvement to the user score to be derived from an identified enhancement to a cost of implementing the identified enhancement. The user is provided an ordered list of the identified enhancements organized by the relative cost benefit measure of each of the identified enhancements.

In another embodiment, the user provides the beauty enhancement processor data relating to a number of body regions, and the beauty enhancement processor provides the user a composite score indicative of the overall beauty of the user. As previously described, the user may request that the composite score be recalculated based on selected enhancement to one or more body regions of the user. Alternatively, the beauty enhancement processor may assess the user data and scores and present the user with an order list of identified enhancements that will improve the user's composite score. In an embodiment, the list is organized by relative improvement in the user score. In still another embodiment, for each of the one or more identified enhancements, the beauty enhancement processor determines a cost benefit measure indicative of a unit of improvement to the user score to be derived from an identified enhancement to a cost of implementing the identified enhancement. The user is provided an ordered list of the identified enhancements organized by the relative cost benefit measure of each of the identified enhancements.

Web server 115 communicates with user datastore 170 to store and retrieve user data, images, results, scores and other related information. In an embodiment, a user is identified by a user identifier. Web server 115 operates with user datastore 170 to permit a user to retrieve previously stored information and to compare the user's scores to the scores of other users identified through the user identifier.

Web server 115 also interacts with beauty quantification processor 120 and with score data archive 160. Score data archive 160 comprises images and scores of celebrities, historical figures, and ideal body components. Web server 115 operates with score data archive 160 to permit a user to compare scores of the user with scores of people and models stored in the score data archive 160.

In an embodiment, web server 115 interacts with advice server 175 to provide suggestions for improving scores. The advice may be provided automatically or a prompt may be displayed to the user offering advice on a particular body region.

The operation of a beautify quantification system is illustrated in the following embodiments. However, the presentation of these embodiments is not meant to be limiting.

Figure 4A:
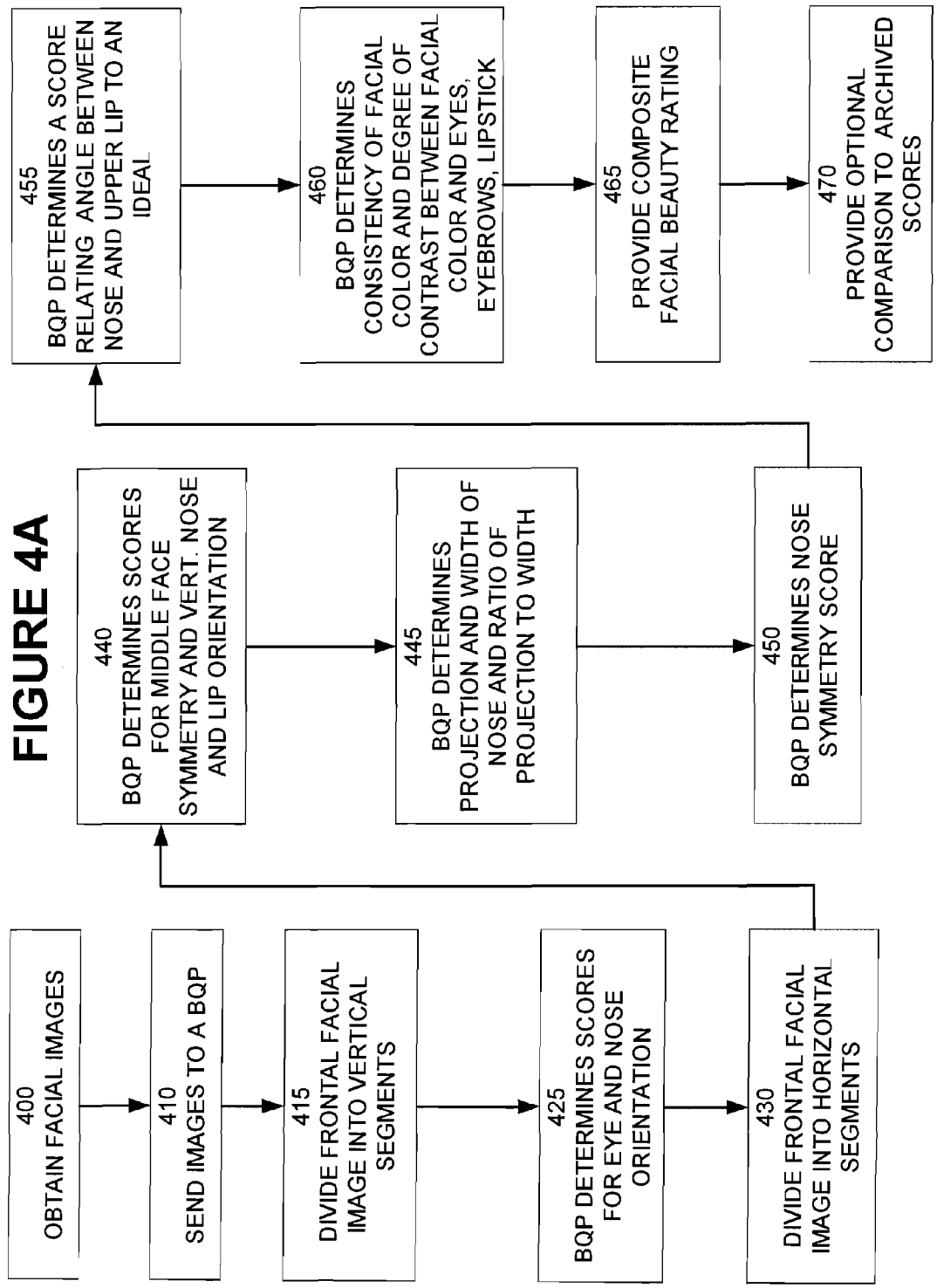
FIG. 4A illustrates the logical flow of a facial evaluation routine according to an embodiment.
Figure 4B:
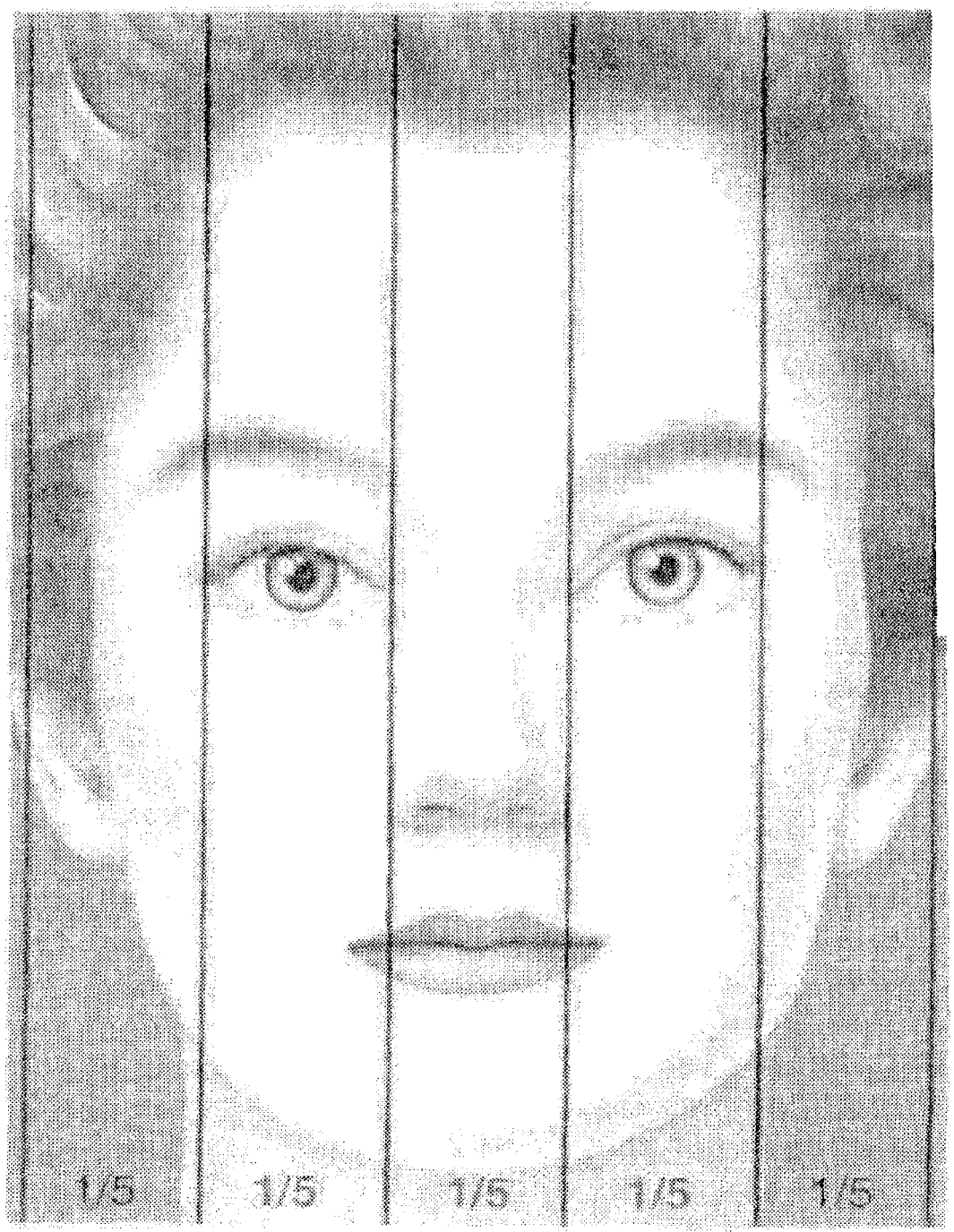
FIGS. 4B-E illustrate geometric proportions used in a facial evaluation routine according to an embodiment.

FIG. 4A illustrates a logical flow of a facial evaluation routine according to an embodiment. Frontal and profile images of the face are taken 400. The images are submitted to a beauty quantification processor 410. The beauty quantification processor divides the frontal facial image into vertical segments 415. (See, FIG. 4B.) By way of illustration, the beauty quantification processor draws vertical lines to mark the horizontal boundaries of the frontal image of the face and four additional vertical lines (six in total) to divide the face into five equally spaced vertical segments. The beauty quantification processor accesses a facial algorithm stored in the facial measures datastore (FIG. 1, 142) and provides scores for eye orientation and nose orientation 425.

Figure 4C:
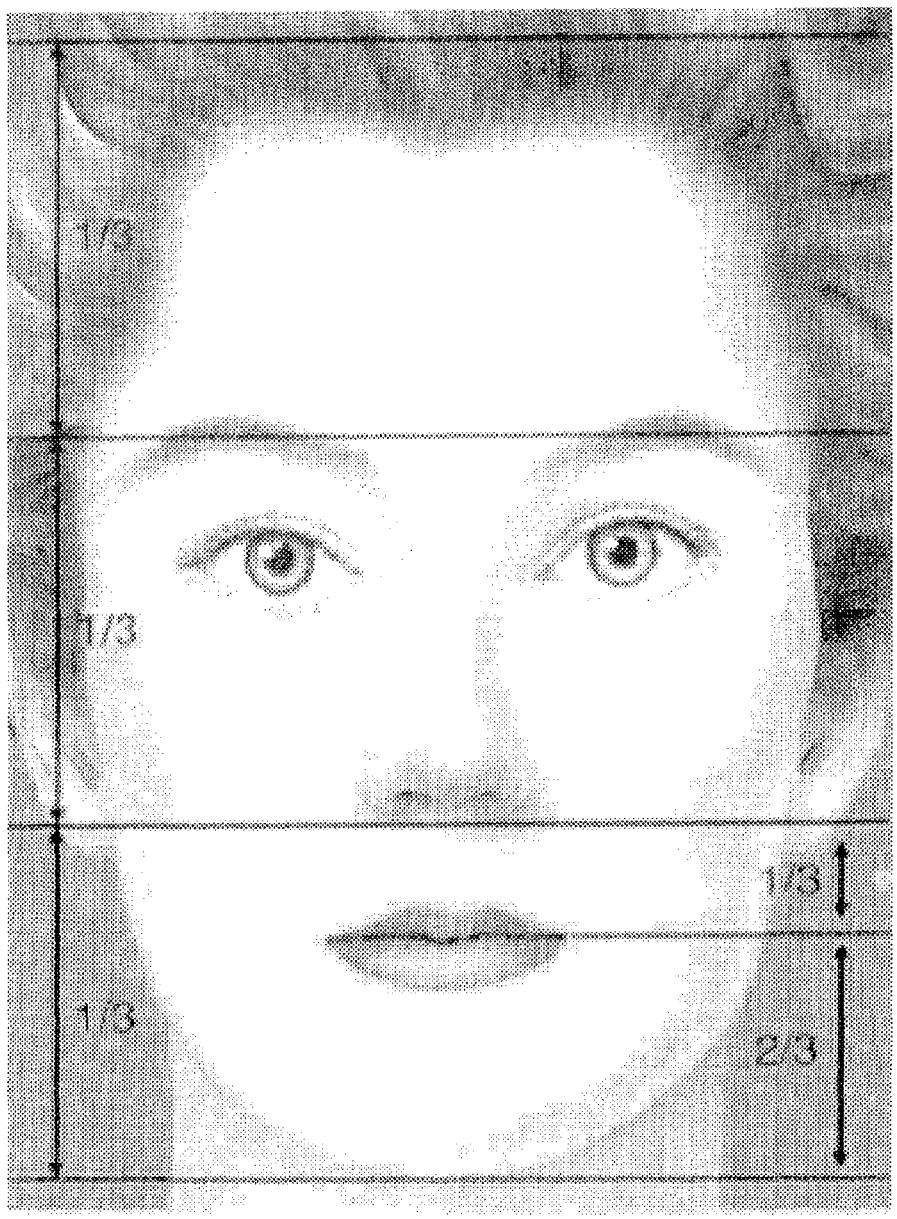

The beauty quantification processor divides the frontal facial image into horizontal segments 430. (See, FIG. 4C.) By way of illustration, the beauty quantification processor draws two horizontal lines to mark the vertical boundaries of the face. A first line marks the top of the head. A second line marks the bottom of the chin. The beauty quantification processor draws two additional horizontal lines (four in total) equally spaced across the frontal image to divide the face into three equal segments. Horizontal lines are also drawn to intersect the corner of the mouth and the bottom of the nose. The beauty quantification processor accesses a facial algorithm and provides scores for middle face symmetry and vertical nose and lip orientation 440.

Figure 4D:
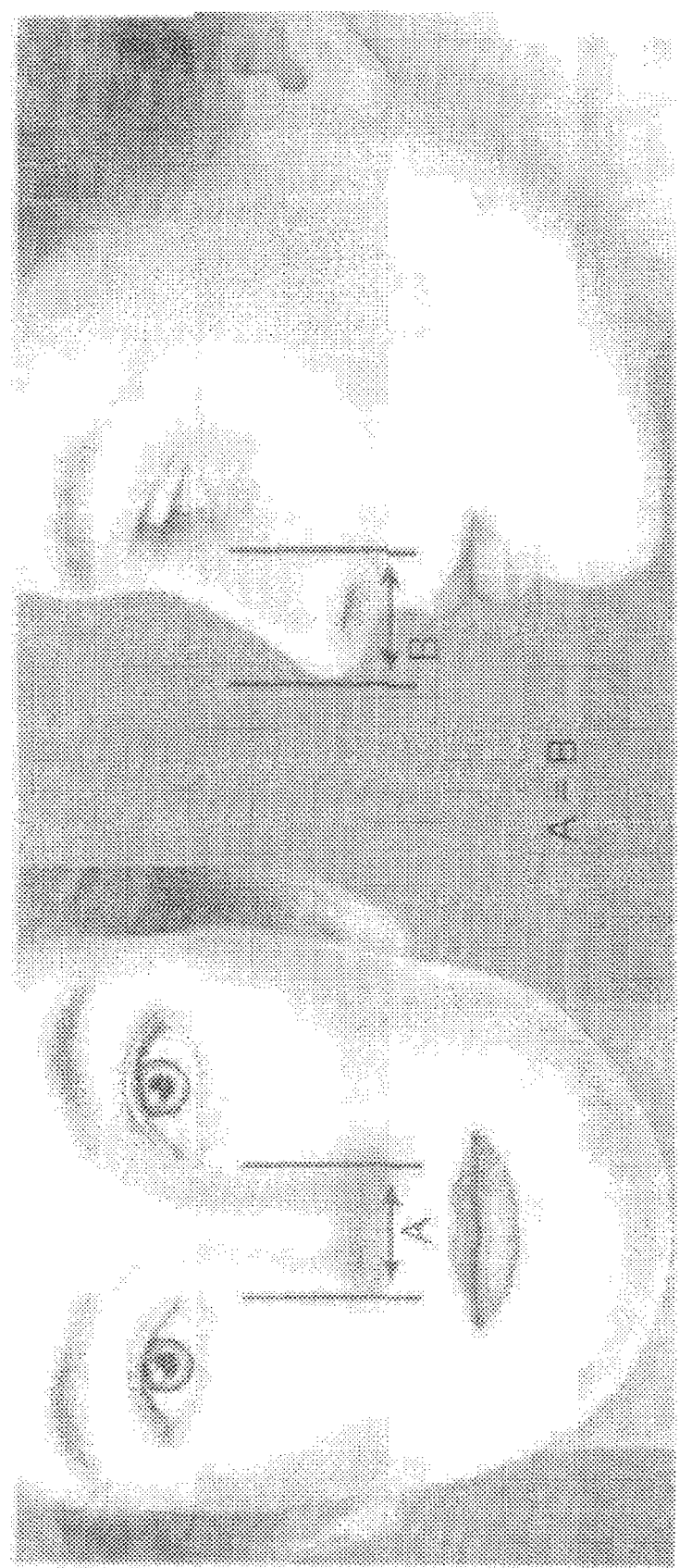
Figure 4E:
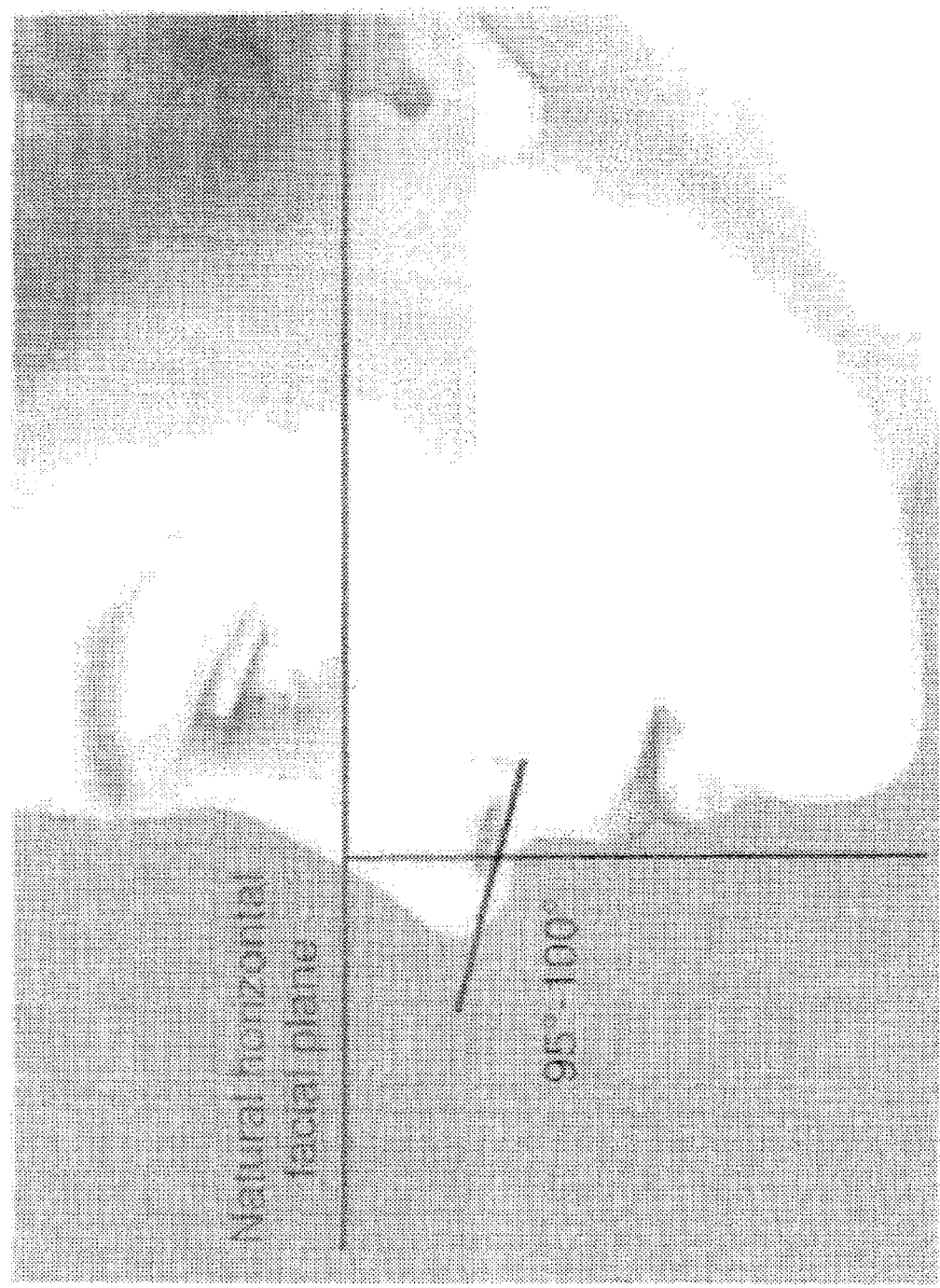

The beauty quantification processor then determines the width and depth of the nose 445. (See, FIG. 4D.) By way of illustration, the beauty quantification processor draws vertical lines delineating the sides of the nose in the frontal image. In the profile image, the beauty quantification processor draws a vertical line delineating the base of the nose and a vertical line that intersects the tip of the nose. The program then determines a nose symmetry score indicative of how close the ratio of projection to width is to one.

In an embodiment, the beauty quantification processor also draws a line (not illustrated) from the bridge of the nose to the tip of the nose. The length of this line corresponds to the length of the nose. The ideal ratio of the length of the nose to the width of the nose is $\phi$.

The beauty quantification processor determines an angle between the nose and the upper lip and provides a score relating the measured angle to an ideal 455. In an embodiment, the ideal angle is ninety degrees for males and 105 degrees for females.

The beauty quantification processor determines the consistency of the color of the face and the degree of contrast between the facial coloring and the eyes, eyebrows, and lipstick 460. A composite facial beauty rating is provided 465.

A user may request that the user's scores be compared with scores in a score data archive 470. The score data archive comprises data of celebrities, historical figures, and ideal mouth and teeth configurations. A user may also request that the user's scores be compared with scores archived scores 470.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160. Alternatively, a user may send facial images to BQS 110 for scoring. The photographs and scores may be stored in user datastore 170. The user may then request a comparison of the user's facial scores to the facial scores of the stored images.

Figure 5:
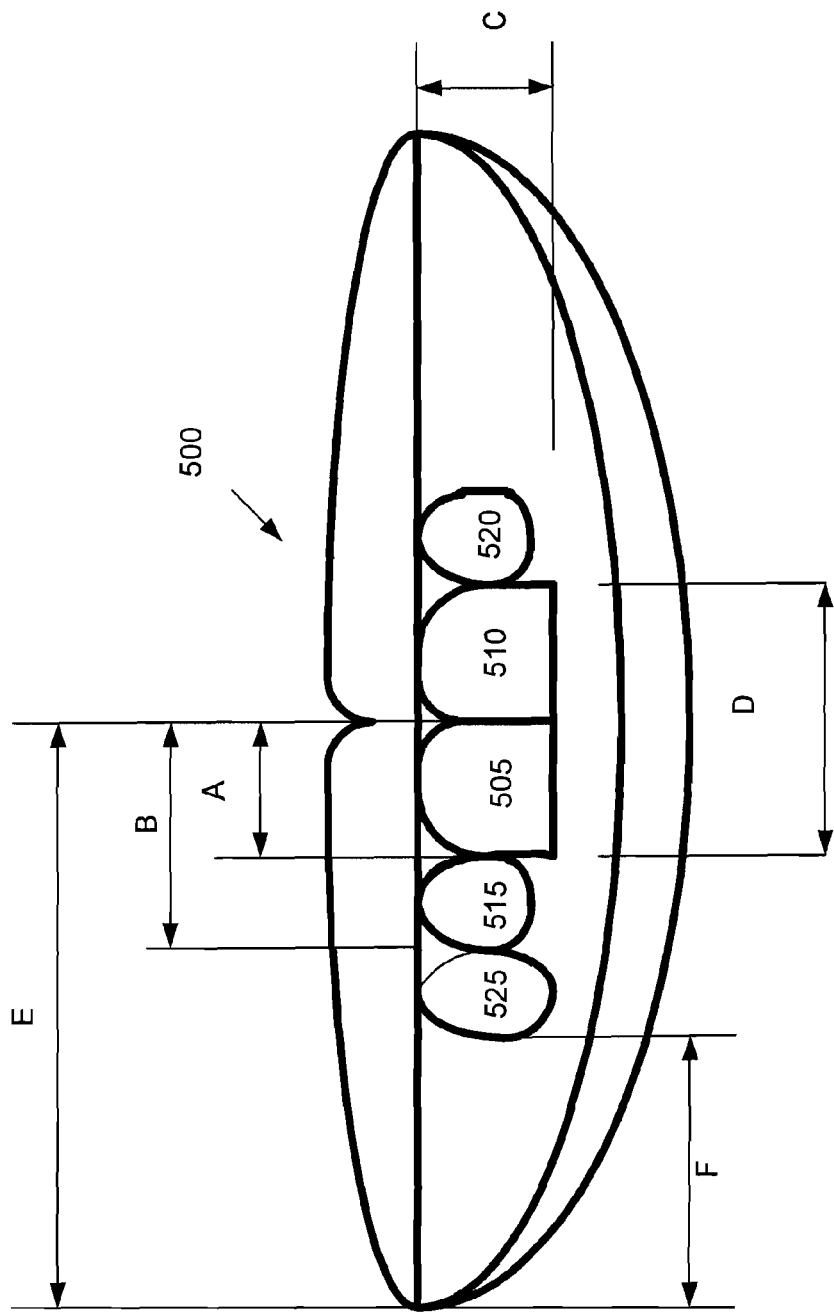
FIG. 5 illustrates parameters for determining the beauty of mouth and teeth according to an embodiment.
Figure 6:
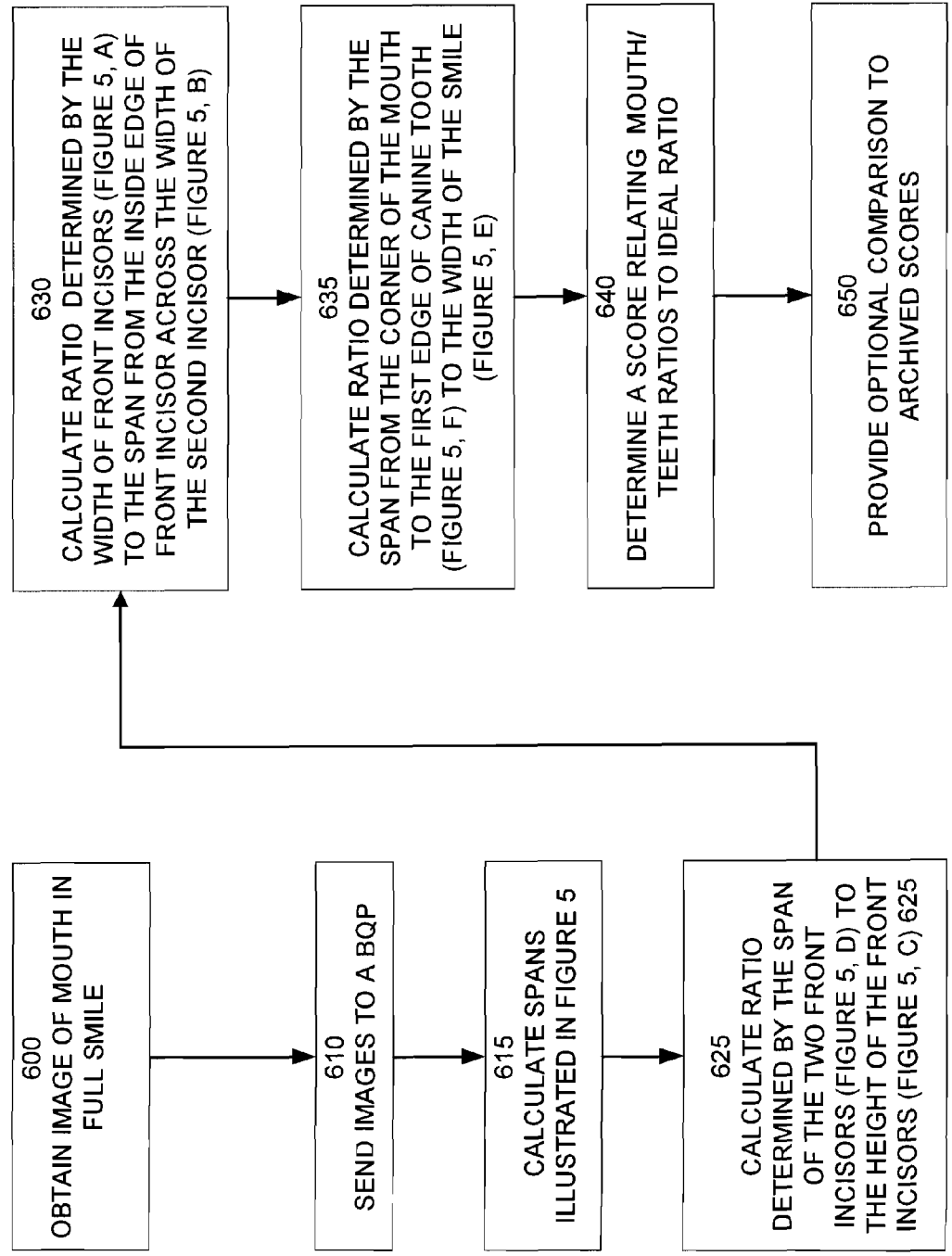
FIG. 6 illustrates a logical flow of mouth/teeth evaluation routine according to an embodiment.

FIG. 5 illustrates parameters for determining the beauty of mouth and teeth according to an embodiment. FIG. 6 illustrates a logical flow of a teeth evaluation routine according to an embodiment.

Referring to FIG. 5, mouth 500 is illustrated with front incisor teeth 505 and 510, second incisors 515 and 520, and right canine 525. Various measurements are indicated as well. Ideally, the front two incisor teeth 505 and 510 form a golden rectangle having a width D and a height C such that the ratio of C/D is equal to $\Phi$. Ideally, the ratio determined by width of front incisor 505 (A) to the span from the inside edge of front incisor 505 across the width of the second incisor 515 (B) is also $\Phi$. Also, the ratio of the span from the corner of the mouth 500 to the first edge of canine tooth 525 (F) to the width of the smile (E) is $\Phi$ as well.

FIG. 6 illustrates a logical flow of mouth/teeth evaluation routine according to an embodiment. A frontal image of the mouth in full smile is taken 600. The image is submitted to a beauty quantification processor 610. The beauty quantification processor computes the spans illustrated in FIG. 5 615. The beauty quantification processor accesses a mouth algorithm and determines a ratio determined by the span of the two front incisors (FIG. 5, D) to the height of the front incisors (FIG. 5, C) 625. The beauty quantification processor also calculates a ratio determined by the width of front incisors (FIG. 5, A) to the span from the inside edge of front incisor across the width of the second incisor (FIG. 5, B) 630. The beauty quantification processor also calculates a ratio determined by the span from the corner of the mouth to the first edge of canine tooth (FIG. 5, F) to the width of the smile (FIG. 5, E). A score is determined based on a comparison of the calculated ratios to a set of ideal ratios 640.

A user may request that the user's scores be compared with scores in a score data archive 650. The score data archive comprises data of celebrities, historical figures, and ideal mouth and teeth configurations.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160. Alternatively, a user may send images of mouths and teeth to BQS 110 for scoring. The photographs and scores may be stored in user datastore 170. The user may then request a comparison of the user's mouth/teeth scores to the mouth/teeth scores of the stored images.

Figure 7:
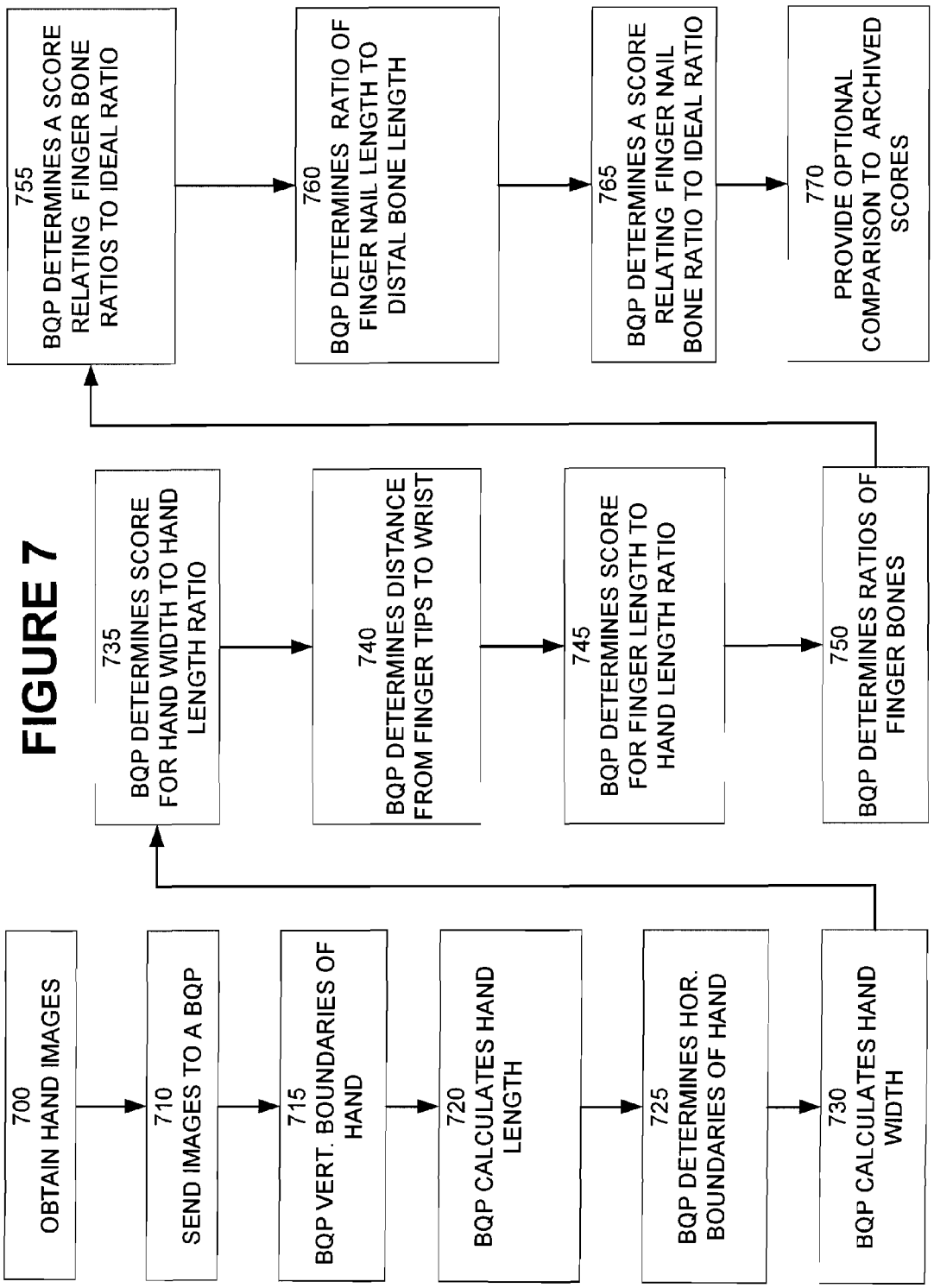
FIG. 7 illustrates the logical flow of a hand evaluation routine according to an embodiment.

FIG. 7 illustrates the logical flow of a hand evaluation routine according to an embodiment. Images of the front of the hand (palm) and the back of the hand (dorsum) are created 700. In an embodiment, the images of the hands are produced by scanning using crumpled aluminum foil as a background. In another embodiment, the images are created using a camera. The images are submitted to a beauty quantification processor 710.

The beauty quantification processor accesses the palm view and draws a line perpendicular at the top of the longest finger and a line parallel to the first at the base of the hand 715. The beauty quantification processor calculates the distance between these lines to determine the hand length 720.

The beauty quantification processor accesses the dorsal view of the same hand and draws a line parallel to the narrowest portion of the right on the "pinky" finger side and a line between the thumb and the index finger that is parallel to the fingers and that marks the broadest part of the hand 725. The beauty quantification processor calculates the distance between these lines to determine the hand width 730.

The beauty quantification processor calculates a ratio of the hand width to the hand length and assigns this ratio a score relating the measured ratio to an ideal ratio 735.

Using the dorsal view, the beauty quantification processor determines the distance between the tips of each of the five fingers and the wrist 740. The beauty quantification processor calculates the ratio of finger length to hand length and assigns a score relating the measured ratio to an ideal ratio 745.

Using the dorsal view, the beauty quantification processor measures the length of each segment of a finger bone and determines a set of ratios for each finger: distal/middle; middle/proximal; proximal/base 750. The beauty quantification processor compares these ratios to Φ and assigns a score relating the measured ratio to the ideal ratio 755.

In an embodiment, the beauty quantification processor identifies whether a particular finger or a particular set of joints is far from the ratio and provides advice on how to make features appear longer or shorter.

The beauty quantification processor determines the distance between the base and tip of each finger nail and determines a ratio of this length to the length of the most distal bone of the finger 760. The beauty quantification processor a score relating the measured ratio to an ideal ratio 765.

Optionally, the beauty quantification processor may adjust a score based on additional information obtained from a user. By way of illustration and not as a limitation, the user may be asked:

Do you bite your nails?
Do you chip away at your cuticles?"
Are your nails painted?

The beauty quantification processor may lower scores for affirmative answers and raise them for negative answers.

The beauty quantification processor may also take into consideration a nail's natural appearance. Thus, if a user indicates that the nails have not been painted, the scores may be elevated for naturally "pink" nails in women, lowered for naturally "blue" discoloration at the base of nails, and lowered for thin brown linear streaks in the nails of patients).

In another embodiment, the beauty quantification processor identifies other features of the hands that may affect the scores. By way of illustration, prominent hair that covers knuckles or the distal phalanxes may result in lower scores. Similarly, obvious joint abnormalities and crooked or missing fingers may result in lower scores. The presence of aging spots, signs of actinic solar purpura, punctate hypopigmentation, papules, smoking stains, wrinkles, thin or thick skin, swollen fingers, and fleshiness or boniness may also lower scores. The presence of protruding tendons and veins may lower the scores of females and raise the scores of males.

In an embodiment, a user may select hands from a data score archive 770 and request that the user's scores be compared with scores of the selected hands. The score data archive comprises data of celebrities, historical figures, and hand configurations.

Referring again to FIG. 1, in an embodiment a user may also request that the user's hand scores be compared with hand scores of other users in datastore 170. In an embodiment, a user may access another user's hand data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160. Alternatively, a user may send images of hands to BQS 110 for scoring. The photographs and scores may be stored in user datastore 170. The user may then request a comparison of the user's hand scores to the hand scores of the stored images.

Figure 8:
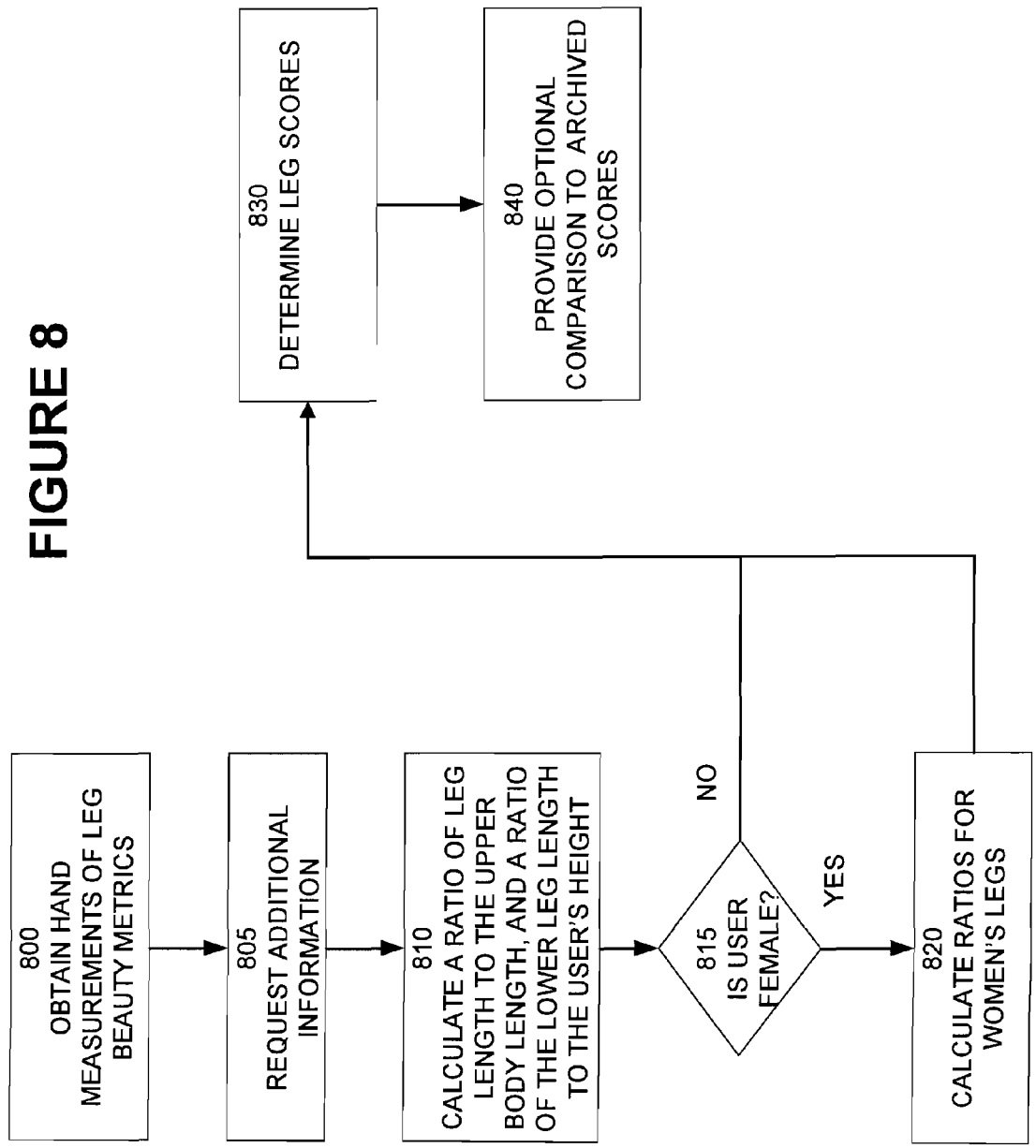
FIG. 8 illustrates the logical flow of a leg evaluation routine according to an embodiment.

FIG. 8 illustrates the logical flow of a leg evaluation routine according to an embodiment. Measurements related to beauty score of the legs are obtained 800. In an embodiment, the following measurements are acquired:

above ankle circumference;
ankle width (frontal view)
ankle width (side view);
calf circumference;
thigh circumference;
lower leg length;
leg length;
height; and
upper body length.

The user may be asked for additional information regarding the user and the condition of the legs 805. In an embodiment, the following additional information is requested:

gender;
do you have spider veins? Is your leg complexion consistent?
What is shape of the heel?

Regarding the heel shape, a user may be presented with images of heel shapes and asked to select a shape that most closely corresponds to the user's heel.

The beauty quantification processor calculates a ratio of leg length to the upper body length, and a ratio of the lower leg length to the user's height 810.

A determination is made whether the user is female 815. If the user is female, the beauty quantification processor calculates 820:

(a) a ratio of the calf circumference to the height of lower leg;
(b) a ratio of the ankle circumference to calf circumference;
(c) a ratio of the ankle side width to the calf circumference divided by π (3.1416);
(d) a ratio of the ankle front width to the calf circumference divided by π;

Leg scores are determined in accordance with a scoring algorithm 830.

In an embodiment, a beauty measures datastore (FIG. 1, 140) comprises leg measures (FIG. 1, 150). In this embodiment, the ideal ratio of the calf circumference to the height of lower leg is determined to be 0.75 in women. Legs having a larger ratio appear too muscular, while legs having a smaller ratio may appear too scrawny. The ideal ratio of the ankle circumference to calf circumference is determined to be 0.63. The ideal ratio of the ankle side width to the calf circumference divided by π is determined to be 0.70. The ideal ratio of ratio of the ankle front width to the calf circumference divided by π is determined to be 0.50.

According an embodiment, for women, the ratio of leg length to the upper body length is ideally about 1.4. Longer is still appealing. However, attractiveness decreases with the ratio. For men, the ratio of leg length to the upper body length is ideally about 1.0. This creates a more muscular appearance. Attractiveness of male legs declines in both directions.

According to an embodiment, for a woman, the ideal ratio of the lower leg length to the user's height is determined to be 0.26. Divergence from this ideal ratio decreases beauty.

A user may request that the user's scores be compared with scores in a score data archive 840. The score data archive comprises data of celebrities, historical figures, and ideal leg configurations.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160. Alternatively, a user may send images of mouths and teeth to BQS 110 for scoring. The photographs and scores may be stored in user datastore 170. The user may then request a comparison of the user's leg scores to the leg scores of the stored images.

Figure 9:
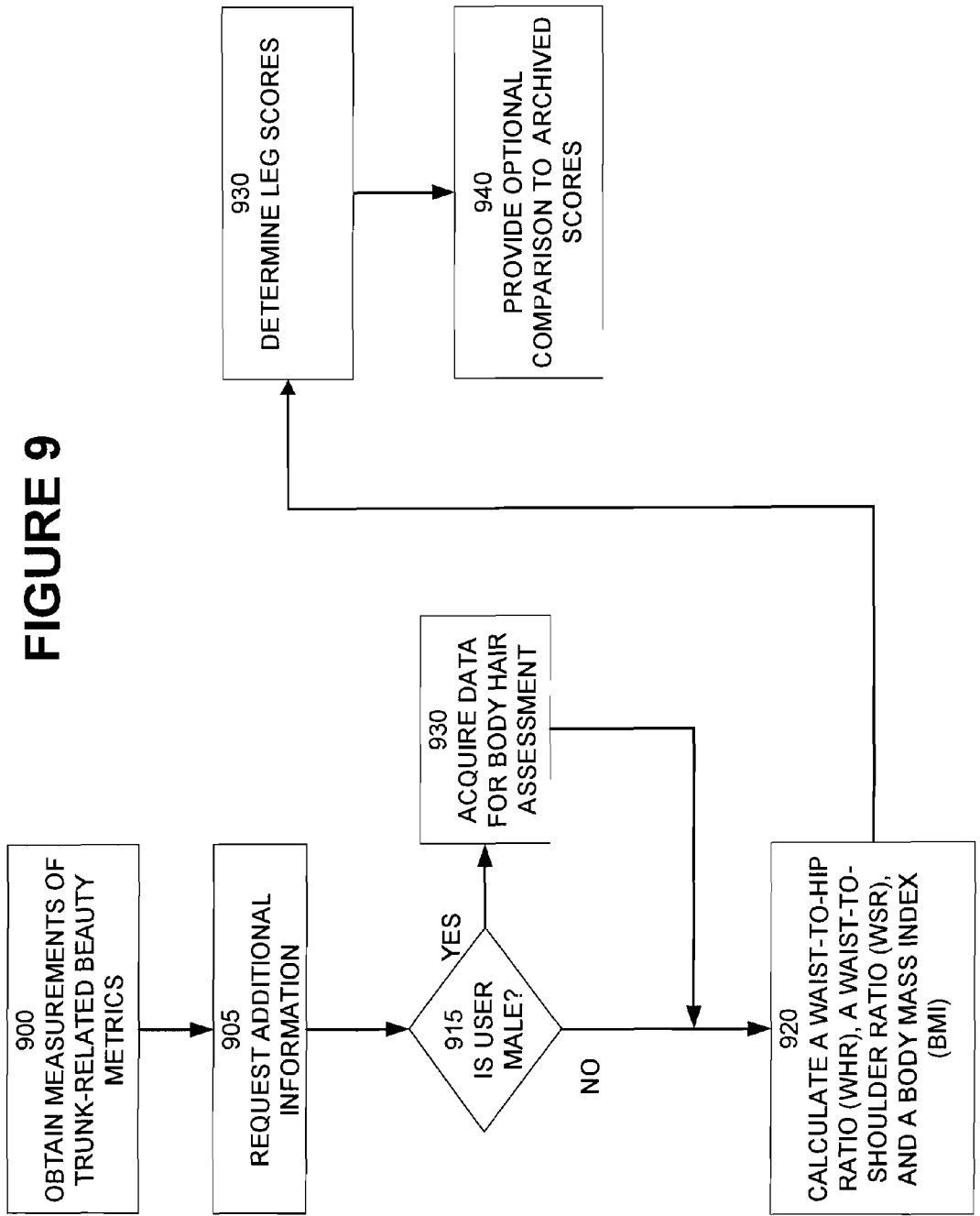
FIG. 9 illustrates the logical flow of a trunk evaluation routine according to an embodiment.

FIG. 9 illustrates the logical flow of a trunk evaluation routine according to an embodiment. Measurements related to a beauty score of the trunk are obtained 900. In an embodiment, the following measurements are acquired:
waist circumference
hip circumference
shoulder circumference
height
weight.

Additional information is acquired 905. In an embodiment, this information comprises:
gender; and a
muscle index.

In an embodiment, the muscle index is acquired by presenting images reflecting different musculatures to the user. For example, images ranging from a body builder's physique (i.e., muscle definition apparent at a distance on abdomen, back and arms) to an individual without discernible muscle definition may be presented. The user selects the image that represents their current physical attributes.

A determination is made if the user is a male 915. If the user is male, the user is asked for a body hair assessment 920. In an embodiment, the body hair assessment is accomplished by presenting images reflecting different degrees of body hair coverage. Again, the user selects the image that most closely matches the user's body condition. The beauty quantification processor calculates a waist-to-hip ratio (WHR), a waist-to-shoulder ratio (WSR), and a body mass index (BMI) 925. Trunk beauty scores are determined in accordance with a scoring algorithm 930.

A user may request that the user's scores be compared with scores in a score data archive 940. The score data archive comprises data of celebrities, historical figures, and ideal leg configurations.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160.

In an embodiment, a beauty measures datastore (FIG. 1, 140) comprises trunk measures (FIG. 1, 154). In this embodiment, the ideal WHR for a female is in the range of 0.67-0.74. A range of 0.75 to 0.83 is considered attractive, 0.84-0.92 is considered good, and 0.93-1.05 is considered acceptable. Below 0.67 and above 1.05 are deemed to be in the unattractive range.

In an embodiment, the ideal WHR for a male that is either muscular or average is in the range of 0.78-0.85. A range of 0.86-0.95 is considered attractive. Below 0.77 and above 0.95 are deemed to be in the unattractive range. The ideal WHR for a male that scrawny is in the range of 0.85-0.95. A range of 0.96-1.1 is considered attractive. Below 0.96 and above 1.1 are deemed to be in the unattractive range.

In an embodiment, the WSR for a female user may be compared to other famous persons or to friends. In some cases, there may not be any ideal ratio or such things as WSR for women, however, this does not mean that a comparison cannot be done to one or more people in whom a user has interest. Indeed, this aspect of comparison to famous persons and friend is anticipated with each measurement region of the various embodiments described herein.

In an embodiment, the ideal WSR for a male that is either muscular or average is in the range of 0.58-0.63. A range of 0.64-0.67 considered attractive. Below 0.58 and above 0.67 are deemed to be in the unattractive range. The ideal WHR for a male that scrawny is in the range of 0.75-0.83. A range 0.84-1.1 is considered attractive. Below 0.75 and above 1.1 are deemed to be in the unattractive range.

In an embodiment, the advice server (FIG. 1, 175) creates a prompt for advice when a user beauty scores are above or below a certain range. For example, a female who has a WHR=0.84-0.92 may be given advice on how to exercise to reduce her WHR. A female with a WHR=0.92-1.05 may receive exercise and dietary advice. A female with a WHR<0.xx may be told to consult a doctor as the ratio is indicative of a potentially significant health condition.

Figure 10:
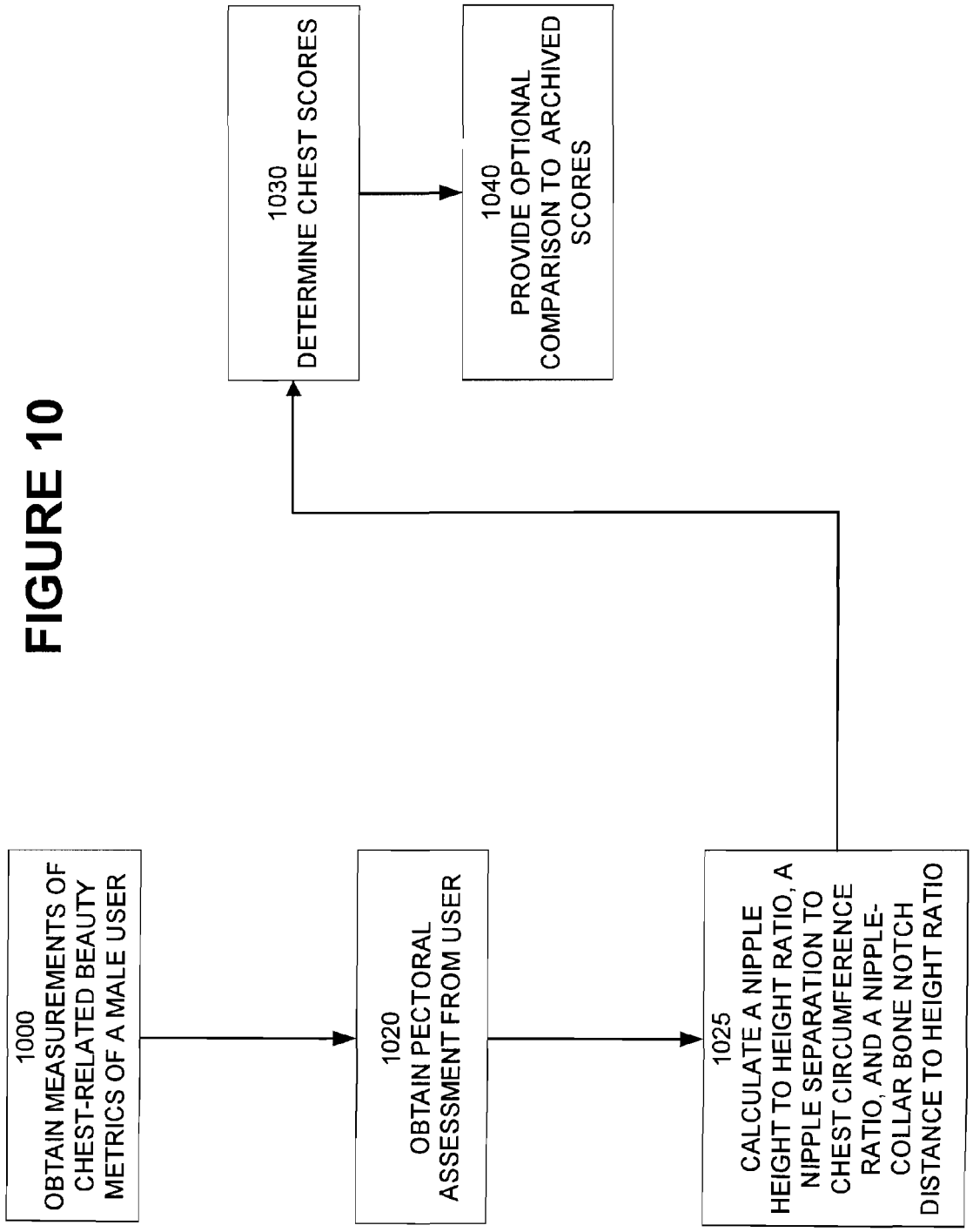
FIG. 10 illustrates the logical flow of a chest evaluation routine for a male user according to an embodiment.

FIG. 10 illustrates the logical flow of a chest evaluation routine for a male user according to an embodiment. Measurements related to a beauty score of the chest are obtained 1000. In an embodiment, the following measurements are acquired for a male user:
distance between the nipples
chest circumference
height
height of nipples from the ground
the distance between each nipple and the notch where the neck muscles meet the collar bone.

The user is asked for a pectoral condition assessment 1020. In an embodiment, the pectoral condition assessment is accomplished by presenting images reflecting different degrees of definition of the pectoral muscles. For example, and not as a limitation, the user may be presented with three options—well defined pectoral muscles, undefined pecs, and flabby chest. The user is prompted to select a graphic that most closely approximates the user's pectoral condition.

Based on the graphic selected, the system applies a value that is stored for later use in scoring or selecting advice to feed back to a user.

The beauty quantification processor uses the measurement data to calculate a nipple height to height ratio, a nipple separation to chest circumference ratio, and a nipple-collar bone notch distance to height ratio 1025. Chest beauty scores are determined in accordance with a scoring algorithm 1030.

A user may request that the user's scores be compared with scores in a score data archive 1040. The score data archive comprises data of celebrities, historical figures, and ideal leg configurations.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160.

In an embodiment, a male user receives a score based on nipple height. A beauty measures datastore (FIG. 1, 140) comprises chest measures (FIG. 1, 144). In this embodiment, beauty quantification process 120 uses chest algorithms to determine the ideal nipple height for a male the height of the user. In an embodiment, an average nipple height=(0.668× height)+9.491 (cm) is considered attractive. If the male user's nipple height is within one standard deviation of this average, then the male user receives a score of 10/10 for nipple height. One standard deviation is 0.012× height (cm). Two points are subtracted from the ideal nipple height score for every standard deviation (down to 0/10).

In an embodiment, the male user is given a score based on the distance between the nipples. In an embodiment, the average distance between nipples=(0.190×chest circumference)+2.192 (cm). This is considered attractive. The beauty quantification processor determines the ideal nipple distance for a male user having the chest circumference of the user. If the nipple distance is within one standard deviation of this average, the male user receives a score of 10/10 for nipple distance. One standard deviation is 0.014× circumference (cm). Two points are subtracted from the ideal nipple distance score for every standard deviation (down to 0/10).

In an embodiment, an average notch-to-nipple distance= (0.120×height)−2.782 (cm) is considered attractive. The beauty quantification processor determines the ideal notch-to-nipple distance for a male user having the height of the user. If his notch-to-nipple distance is within one standard deviation of this average, then the user receives a score of 10/10 for notch-to-nipple distance. One standard deviation is 0.008× height (cm). Two points are subtracted from the ideal notch-to-nipple distance score for every standard deviation (down to 0/10).

Figure 11:
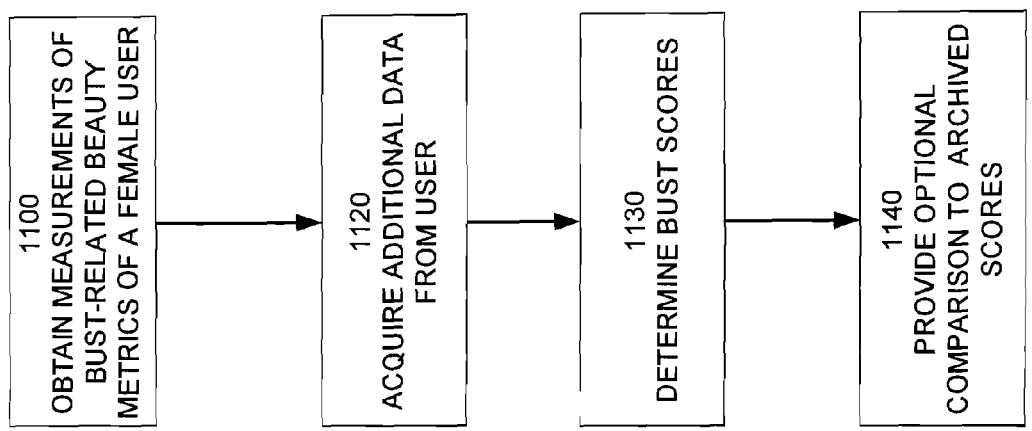
FIG. 11 illustrates that logical flow of a bust evaluation routine for a female user according to an embodiment.

FIG. 11 illustrates that logical flow of a bust evaluation routine for a female user according to an embodiment. Measurements related to a beauty score of the bust are obtained 1100. In an embodiment, the following measurements are acquired for a female user:

circumference of chest just below the bust line
circumference of the chest just above the bust line
circumference of the broadest part of the bust while wearing a bra that is not a push-up bra.

The user is asked for additional information 1020. In an embodiment, the additional information comprises:

bra size;
characterization of breasts as symmetrical in terms of position, color, texture, and size;
characterization of whether chest is softly curved or angular;
characterization of the whether the chest feels "soft" when the female user hugs another person; and
characterization as to whether the female user is satisfied with the size of her bust.

The beauty quantification processor uses the measurement data to calculate a "bust score" using a scoring algorithm 1130.

A user may request that the user's scores be compared with scores in a score data archive 1140. The score data archive comprises data of celebrities, historical figures, and ideal leg configurations.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160.

In an embodiment, the beauty quantification processor uses the measurement data to calculate an appropriate bra size and compares it with the size entered by the female user. If the two answers do not match, then the visitor is advised. The computer may then compare this size to the "ideal" bust of the decade (or some similar standard), noting that the ideal bust size is something that changes with societal whim.

FIG. 12 illustrates the logical flow of a foot evaluation routine for user according to an embodiment. Measurements related to a beauty score of the foot are obtained 1200. In an embodiment, the following measurements are obtained:

length of each foot as measured from the hard bone at the heel to the tip of the longest toe; and
a height measure taken while standing erect.

Additional information is obtained from the user 1220. In an embodiment, the following additional information is obtained:

an arch assessment, i.e., normal or fallen;
male or female;
length
width of shoe size;
appearance of nail fungus, thick nails, ingrown nails, nail discoloration, hammertoes, bunions, corns, calluses, warts, cracked/dried heels, foot redness or irritation, clubfeet, spurs, moist feet, and whether nails are painted and/or polished. In an embodiment, the presence of any of these conditions with the exception of painted/polished nails lowers the foot beauty score.

The computer program associated with one embodiment calculates the ratio of foot length to height 1225. A foot beauty score is calculated 1230.

A user may request that the user's scores be compared with scores in a score data archive 1240. The score data archive comprises data of celebrities, historical figures, and ideal leg configurations.

Referring again to FIG. 1, in an embodiment, a user may also request that the user's scores be compared with scores of other users in datastore 170. In an embodiment, a user may access another user's data in user datastore 170 only if the user knows the user identifier of the other user. Score data archive 160 comprises images and scores of celebrities, historical figures, and ideal body components. In an embodiment, a user may also request that the user's scores be compared with scores of people and models stored in the score data archive 160.

In an embodiment, a foot Length/Height ratio (expressed as a percentage) of 15% is average. However, for women, the ideal foot is slightly smaller than average (around 14.5% of her height). Thus, 14.25-14.75% receives a score of 10 out of 10 for foot length. Women with feet in the 13.5-14.25% range receive a score of 8 out of 10 for foot length. Women with feet smaller than 13.5% receive a score of 5/10 for foot length. Women with feet in the 14.75-15.25% range receive a score of 8/10 for foot length. Women with feet in the 15.25-16.5% range receive a score of 7/10 for foot length. Women above the 16.5% range receive a score of 4/10 for foot length.

For men, the ideal foot is of average length. Thus, 14.5-15.5% receives a score of 10/10 for foot length. However, other rating may be assigned as follows: Men with feet in the 13.5-14.5% range receive a score of 8 out of 10 for foot length. Men with feet smaller than 13.5% receive a score of 4/10 for foot length. Men with feet in the 15.5-16.5% range receive a score of 7/10 for foot length. Men with feet in the 16.5-17.5% range receive a score of 5/10 for foot length. Men above the >17.5% range receive a score of 3/10 for foot length.

It will be understood by those skilled in the art that the present invention may be, without limitation, embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular. Moreover, a reference to a specific time, time interval, and instantiation of scripts or code segments is in all respects illustrative and not limiting.

What is claimed is:

1. A beauty quantification system comprising:
    a beauty quantification processor;
    a beauty measure datastore, wherein the beauty measure datastore comprises quantifiable measures of beauty of a body region;
    a beauty score datastore;
    a user computing device;
    a network; and
    a beauty enhancement processor,
    wherein the beauty quantification processor comprises instructions for:
        receiving user data indicative of physical attributes of a selected body region of the user;
        obtaining measures of beauty from the beauty measures datastore associated with the selected body region;
        evaluating the user data against the beauty measures of the selected body region;
        determining a user score indicative of the beauty of the selected body region of the user;
        storing the user score in the beauty score datastore; and
        comparing the user score to a score stored in the beauty score datastore; and
    wherein the beauty enhancement processor comprises instructions for:
        receiving from the user a selection for an enhancement of the selected body region;
        applying the selected enhancement to the selected body region; and
        determining an enhanced user score indicative of the beauty of the selected body region after application of the selected enhancement.

2. The system of claim 1, wherein the body region is selected from the group consisting of a face, a chest, feet, arms, legs, buttocks, a trunk, teeth, a mouth, eyes, hands, hair, and fingers.

3. The system of claim 1 wherein the measures of beauty are selected from the group consisting of facial measures, chest measures, foot measures, arm measures, leg measures, buttocks measures, trunk measures, teeth measures, mouth measures, eyes measures, hands measures, hair measures, and finger measures.

4. The system of claim 1, wherein the score stored in the beauty score datastore is a score selected from the group consisting of a score of another user, a score of a public figure, and a score of an ideal person.

5. The system of claim 1, wherein the selected enhancement is selected from the group consisting of adding glasses, removing glasses, adding makeup, changing a makeup color and shade, changing a hair style, adding facial hair, removing facial hair, changing the size of a body part, and changing the shape of a body part.

6. The system of claim 1 wherein the beauty enhancement processor further comprises instructions for comparing the enhanced user score to a score stored in the beauty score datastore.

7. The system of claim 6, wherein the score stored in the beauty score datastore is a score selected from the group consisting of a score of another user, a score of a public figure, and a score of an ideal person.

8. A beauty quantification system comprising:
    a beauty quantification processor;
    a beauty measure datastore, wherein the beauty measure datastore comprises quantifiable measures of beauty of a body region;
    a beauty score datastore;
    a user computing device;
    a network; and
    a beauty enhancement processor,
    wherein the beauty quantification processor comprises instructions for:
        receiving user data indicative of physical attributes of a selected body region of the user;
        obtaining measures of beauty from the beauty measures datastore associated with the selected body region;
        evaluating the user data against the beauty measures of the selected body region;
        determining a user score indicative of the beauty of the selected body region of the user;
        storing the user score in the beauty score datastore; and
        comparing the user score to a score stored in the beauty score datastore; and
    wherein the beauty enhancement processor further comprises instructions for:
        evaluating the selected body region for enhancement;
        identifying one or more enhancements to apply to the selected body region to improve the user score; and
        determining an enhanced user score indicative of the beauty of the selected body region after application of each of the one or more identified enhancements.

9. The system of claim 8, wherein the one or more identified enhancements are selected from the group consisting of adding glasses, removing glasses, adding makeup, changing a makeup color and shade, changing a hair style, adding facial hair, removing facial hair, changing the size of a body part, and changing the shape of a body part.

10. The system of claim 8, wherein the beauty enhancement processor further comprises instructions for providing the user an ordered list of the one or more identified enhancements organized by relative improvement in the user score.

11. The system of claim 8, wherein the beauty enhancement processor further comprises instructions for;
for each of the one or more identified enhancements, determining a cost benefit measure indicative of a unit of improvement to the user score to be derived from an identified enhancement to a cost of implementing the identified enhancement; and
providing the user an ordered list of the one or more identified enhancements organized by relative cost benefit measure of each of the one or more identified enhancements.

12. The system of claim 11, wherein the one or more identified enhancements are selected from the group consisting of adding glasses, removing glasses, adding makeup, changing a makeup color and shade, changing a hair style, adding facial hair, removing facial hair, changing the size of a body part, and changing the shape of a body part.

13. A beauty quantification system comprising:
a beauty quantification processor;
a beauty measure datastore, wherein the beauty measure datastore comprises quantifiable measures of beauty of a plurality of body regions;
a beauty score datastore;
a user computing device;
a network; and
a beauty enhancement processor,
wherein the beauty quantification processor comprises instructions for:
receiving user data indicative of physical attributes of the plurality of body regions of the user;
obtaining measures of beauty from the beauty measures datastore associated with each of the plurality of body regions;
evaluating the user data against the beauty measures of each of the plurality of body regions;
determining a composite user score indicative of the beauty of the user;
storing the user score in the beauty score datastore; and
comparing the user score to a score stored in the beauty score datastore; and,
wherein the beauty enhancement processor comprises instructions for:
receiving from the user a selection for an enhancement of a body region selected from the plurality of body regions;
applying the selected enhancement to the selected body region; and
determining an enhanced composite user score indicative of the beauty of the user after application of the selected enhancement.

14. The system of claim 13, wherein the body plurality of body regions is selected from the group consisting of a face, a chest, feet, arms, legs, buttocks, a trunk, teeth, a mouth, eyes, hands, hair, and fingers.

15. The system of claim 13, wherein the measures of beauty are selected from the group consisting of facial measures, chest measures, foot measures, arm measures, leg measures, buttocks measures, trunk measures, teeth measures, mouth measures, eyes measures, hands measures, hair measures, and finger measures.

16. The system of claim 13, wherein the score stored in the beauty score datastore is a score selected from the group consisting of a score of another user, a score of a public figure, and a score of an ideal person.

17. The system of claim 14, wherein the selected enhancement is selected from the group consisting of adding glasses, removing glasses, adding makeup, changing a makeup color and shade, changing a hair style, adding facial hair, removing facial hair, changing the size of a body part, and changing the shape of a body part.

18. The system of claim 14, wherein the beauty enhancement processor further comprises instructions for comparing the enhanced user score to a score stored in the beauty score datastore.

19. The system of claim 18, wherein the score stored in the beauty score datastore is a score selected from the group consisting of a score of another user, a score of a public figure, and a score of an ideal person.

20. A beauty quantification system comprising:
a beauty quantification processor;
a beauty measure datastore, wherein the beauty measure datastore comprises quantifiable measures of beauty of a plurality of body regions;
a beauty score datastore;
a user computing device;
a network; and
a beauty enhancement processor,
wherein the beauty quantification processor comprises instructions for:
receiving user data indicative of physical attributes of the plurality of body regions of the user;
obtaining measures of beauty from the beauty measures datastore associated with each of the plurality of body regions;
evaluating the user data against the beauty measures of each of the plurality of body regions;
determining a composite user score indicative of the beauty of the user;
storing the user score in the beauty score datastore; and
comparing the user score to a score stored in the beauty score datastore; and
wherein the beauty enhancement processor further comprises instructions for:
evaluating each of the plurality of body regions for enhancement;
identifying one or more enhancements to apply to each one of the plurality of body regions to improve the user composite score; and
determining an enhanced user score indicative of the beauty of the user after application of each of the one or more identified enhancements.

21. The system of claim 20, wherein the one or more identified enhancements are selected from the group consisting of adding glasses, removing glasses, adding makeup, changing a makeup color and shade, changing a hair style, adding facial hair, removing facial hair, changing the size of a body part, and changing the shape of a body part.

22. The system of claim 20, wherein the beauty enhancement processor further comprises instructions for providing the user an ordered list of the one or more identified enhancements organized by relative improvement in the user composite score.

23. The system of claim 20, wherein the beauty enhancement processor further comprises instructions for;
for each of the one or more identified enhancements, determining a cost benefit measure indicative of a unit of improvement to the user composite score to be derived from an identified enhancement to a cost of implementing the identified enhancement; and providing the user an ordered list of the one or more identified enhancements organized by relative cost benefit measure of each of the one or more identified enhancements.

24. The system of claim 23, wherein the one or more identified enhancements are selected from the group consisting of adding glasses, removing glasses, adding makeup, changing a makeup color and shade, changing a hair style, adding facial hair, removing facial hair, changing the size of a body part, and changing the shape of a body part.

25. A beauty quantification system comprising:
a beauty quantification processor;
a beauty measure datastore, wherein the beauty measure datastore comprises quantifiable measures of beauty of a body region;
a beauty score datastore;
a user computing device;
a network; and
a beauty enhancement processor,
wherein the beauty quantification processor comprises instructions for:
receiving user data indicative of physical attributes of a selected body region of the user;
obtaining measures of beauty from the beauty measures datastore associated with the selected body region;
evaluating the user data against the beauty measures of the selected body region;
determining a user score indicative of the beauty of the selected body region of the user;
storing the user score in the beauty score datastore;
comparing the user score to a score stored in the beauty score datastore;
receiving from the user additional information;
applying the additional information to the selected body region; and
determining an adjusted user score indicative of the beauty of the selected body region after application of the additional information.

* * * * *